United States Patent
Lundgreen et al.

(10) Patent No.: US 10,309,950 B2
(45) Date of Patent: *Jun. 4, 2019

(54) TEST-ELEMENT FOR A MOBILE WATER ANALYSIS ARRANGEMENT

(71) Applicant: HACH LANGE GMBH, Berlin (DE)

(72) Inventors: Ulrich Lundgreen, Guetersloh (DE); Aria Farjam, Duessldorf (DE); Rolf Uthemann, Leverkusen (DE); Andreas Mitreiter, Kleinmachnow (DE); Isabel Huenig, Duesseldorf (DE); Markus Lenhard, Viersen (DE); Rainer Froemel, Troisdorf (DE); Hans-Joachim Kumpch, Berlin (DE)

(73) Assignee: HACH LANGE GMBH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/447,138

(22) Filed: Mar. 2, 2017

(65) Prior Publication Data
US 2017/0176406 A1 Jun. 22, 2017

Related U.S. Application Data

(63) Continuation of application No. 14/172,915, filed on Feb. 5, 2014, now Pat. No. 9,625,435, which is a (Continued)

(30) Foreign Application Priority Data

Oct. 6, 2008 (DE) ........................ 10 2008 050 092

(51) Int. Cl.
*G01N 33/18* (2006.01)
*G01N 21/31* (2006.01)
(Continued)

(52) U.S. Cl.
CPC ...... *G01N 33/1893* (2013.01); *B01L 3/50273* (2013.01); *B01L 3/502715* (2013.01); (Continued)

(58) Field of Classification Search
CPC ............... G01N 33/1893; G01N 21/78; G01N 27/4167; G01N 27/4168; G01N 21/3151; (Continued)

(56) References Cited

U.S. PATENT DOCUMENTS 3,699,437 A * 10/1972 Ur ........................ G01N 27/06
324/706
5,386,287 A 1/1995 Berssen et al.
(Continued)

FOREIGN PATENT DOCUMENTS

| CN | 1250160 A | 4/2000 |
|---|---|---|
| DE | 41 09 118 A1 | 9/1992 |

(Continued)

OTHER PUBLICATIONS

"2320 Alkalinity" section of the American Public Health Association's publication Standard Methods (2005).
(Continued)

*Primary Examiner* — Samuel P Siefke
(74) *Attorney, Agent, or Firm* — Norman B. Thot (57) ABSTRACT

A test element for a mobile water analyzing system includes a sample line and a key reagent disposed in the sample line. The sample line includes an inlet opening arranged at a first end, a pump port arranged at a second end of the sample line, an inlet section arranged between the inlet opening and the pump port, and a measuring section with at least one window arranged at an end of the measuring section. The inlet opening receives a water sample. The measuring section is arranged between the inlet section and the pump port and is coincident with a sample pathway.

15 Claims, 8 Drawing Sheets

Related U.S. Application Data continuation of application No. 13/122,560, filed as application No. PCT/EP2009/062521 on Sep. 28, 2009, now Pat. No. 9,012,234.

(51) Int. Cl.
*B01L 3/00* (2006.01)
*G01N 21/78* (2006.01)
*G01N 27/416* (2006.01)

(52) U.S. Cl.
CPC ......... *G01N 21/3151* (2013.01); *G01N 21/78* (2013.01); *G01N 27/4167* (2013.01); *G01N 27/4168* (2013.01); *G01N 33/1886* (2013.01); *B01L 3/5027* (2013.01); *B01L 2300/0645* (2013.01); *B01L 2300/0654* (2013.01); *B01L 2300/0681* (2013.01); *B01L 2300/0838* (2013.01); *B01L 2400/0475* (2013.01); *G01N 2201/0245* (2013.01)

(58) Field of Classification Search
CPC ........ G01N 33/1886; G01N 2201/0245; B01L 3/502715; B01L 3/50273; B01L 2300/0838; B01L 2400/0475; B01L 2300/0654; B01L 2300/0645; B01L 2300/0681; B01L 3/5027

See application file for complete search history.

(56) References Cited

U.S. PATENT DOCUMENTS

| | | | |
|---|---|---|---|
| 5,572,328 A | 11/1996 | Fouckhardt et al. | |
| 5,731,212 A * | 3/1998 | Gavin | B01L 3/502 356/244 |
| 5,821,405 A | 10/1998 | Dickey et al. | |
| 5,844,686 A | 12/1998 | Treptow et al. | |
| 5,993,742 A | 11/1999 | Binz et al. | |
| 6,130,098 A * | 10/2000 | Handique | B01F 5/0085 366/DIG. 2 |
| 6,596,237 B1 | 7/2003 | Borrelli et al. | |
| 7,459,713 B2 | 12/2008 | Coates | |
| 7,491,366 B2 | 2/2009 | Tokhtuev et al. | |
| 9,012,234 B2 * | 4/2015 | Lundgreen | G01N 21/3151 422/400 |
| 9,625,435 B2 * | 4/2017 | Lundgreen | G01N 33/1893 |
| 2004/0098211 A1 | 5/2004 | Binz et al. | |
| 2004/0109790 A1 | 6/2004 | Shartle et al. | |
| 2004/0154933 A1 | 8/2004 | Cosofret | |
| 2005/0037508 A1 | 2/2005 | Hernandez et al. | |
| 2007/0144277 A1 * | 6/2007 | Padmanabhan | B01L 3/502715 73/864.81 |
| 2008/0227185 A1 | 9/2008 | Schonfeld et al. | |
| 2008/0241966 A1 | 10/2008 | Kunnecke et al. | |
| 2008/0265146 A1 | 10/2008 | Coates | |
| 2009/0009768 A1 | 1/2009 | Jiang et al. | |
| 2010/0009336 A1 | 1/2010 | Sullivan | |
| 2011/0212538 A1 | 9/2011 | Lundgreen et al. | |
| 2011/0217213 A1 | 9/2011 | Chen et al. | |
| 2012/0021527 A1 | 1/2012 | Salzer et al. | |
| 2012/0305394 A1 | 12/2012 | Bae et al. | |

FOREIGN PATENT DOCUMENTS

| | | |
|---|---|---|
| DE | 101 26 054 A1 | 6/2002 |
| EP | 0 821 231 A2 | 1/1998 |
| EP | 1 506 813 A1 | 2/2005 |
| EP | 1 764 153 A2 | 3/2007 |
| EP | 1 870 033 A1 | 12/2007 |
| EP | 2 266 691 A1 | 12/2010 |
| WO | WO 02/074043 A2 | 9/2002 |
| WO | WO 2008/137260 A1 | 11/2008 |
| WO | WO 2010/040657 A1 | 4/2010 |

OTHER PUBLICATIONS

Hach Company APA 6000 ™ Alkalinity 2001 Operation Manuel.
J. S. Fritz et al.: "Quantitative Analytical Chemistry", Fifth Edition, Boston, pp. 151-154 (1987).

* cited by examiner

TEST-ELEMENT FOR A MOBILE WATER ANALYSIS ARRANGEMENT

CROSS REFERENCE TO PRIOR APPLICATIONS

This application is a continuation of U.S. patent application Ser. No. 14/172,915, filed on Feb. 5, 2014, which is a continuation of U.S. patent application Ser. No. 13/122,560, filed on May 10, 2011, which is a U.S. National Phase application under 35 U.S.C. § 371 of International Application No. PCT/EP2009/062521, filed on Sep. 28, 2009 and which claims benefit to German Patent Application No. 10 2008 050 092.5, filed on Oct. 6, 2008. The International Application was published in German on Apr. 15, 2010 as WO 2010/040655 A1 under PCT Article 21(2). U.S. patent application Ser. No. 13/122,560 issued as U.S. Pat. No. 9,012,234 on Apr. 21, 2015.

FIELD

The present invention provides a test-element for a mobile water-analyzing system for determining an analyte in a water-sample. "Mobile" means that the water-analyzing system of the present invention is not stationary as a continuously working process analyzing-device.

BACKGROUND

The prior art in the field of mobile water-analysis is currently represented by so-called photometric cuvette tests as described in DE 41 09 118 A1. The use of these tests is performed manually. First, a water-sample is taken by a pipette and given into the cuvette which contains a key-reagent. The cuvette is closed and shaken to mix the water-sample with the key-reagent. It can then be inserted into a photometer and measured.

The handling of such a cuvette test is inconvenient and extremely susceptible to errors. The key-reagent used can be dangerous for health and the environment, so that the used cuvette tests must be disposed in an appropriate way. The inconvenient handling makes the cuvette tests practical only for use in a laboratory.

SUMMARY

An aspect of the present invention is to provide a test-element for a mobile water-analyzing system for determining an analyte in a water-sample with an improved handling.

In an embodiment, the present invention provides a test-element for a mobile water analyzing system which includes a sample line and a key reagent disposed in the sample line. The sample line comprises an inlet opening disposed at a first end, a pump port disposed at a second end of the sample line, an inlet section disposed between the inlet opening and the pump port, and a measuring section comprising at least one window arranged at an end of the measuring section. The inlet opening is configured to receive a water sample. The measuring section is arranged between the inlet section and the pump port and is coincident with a sample pathway.

BRIEF DESCRIPTION OF THE DRAWINGS

The present invention is described in greater detail below on the basis of embodiments and of the drawings in which.

DETAILED DESCRIPTION

In an embodiment of the present invention, the mobile water-analyzing system is provided with a mobile basic unit and a removable disposable test-element which is insertable into the basic unit. The test-element is a complex prefabricated part, whereby the test-element is provided with a sample-line with an inlet opening which is positioned at the distal end of the test-element. A measuring section is provided in line of the sample-line, the sample-line being provided with a measuring track for an analyzer. A pump opening at the other end of the sample-line can furthermore be connected with a pump mimic of a different nature, the pump mimic of the basic unit comprising the pump actuator. The water-sample can be transported in the sample-line in both directions and can be exactly positioned by using the pump actuator or the pump mimic, respectively. All other parts of the analyzer can, for example, be in the basic unit but outside of the test-element.

The test-element is furthermore provided with a key-reagent positioned inside the sample-line, the key-reagent being, for example, in a dry state. The key-reagent can be positioned between the inlet opening and the measuring section or between the measuring section and the pump opening.

The basic unit is provided with a test-element slot for holding the inserted test-element. The basic unit is provided with an analyzer to measure the water-sample inside the measuring section photometrically or electrochemically. The basic unit is also provided with a pump actuator which is connected cooperatively with the pump opening of the inserted test-element. The pump actuator sucks the water-sample into the sample-line and transports the sucked water-sample inside the sample-line.

The determination of an analyte of a water-sample is performed by first inserting a test-element manually or automatically into the basic unit. The inlet opening is then immersed manually into the water to be analyzed and the pump actuator is activated. The activation can be performed manually or automatically. By activation of the pump actuator, a water-sample is pumped through the inlet opening toward the measuring section.

A defined volume of the water-sample is sucked and is segregated as a sample-column whereby the sample column at both ends is terminated by air. By limiting the sample-column with a defined volume, a defined ratio between the water-sample and the key-reagent is provided. In addition, by pumping the segregated water-sample column repeatedly back and forth, the water-sample is mixed with the key-reagent in the sample-line, whereby the contact of the water-sample column with the sample-line wall causes a turbulence flow, so as to provide a homogeneous mixing of the water-sample with the key-reagent.

The limitation of the water-sample portion to a defined portion can be realized by giving the customer a signal after the pump actuator has stopped after sucking a defined volume of the water-sample so that the customer obtains the information that the sampling is finished and that the inlet opening can be taken out of the water to be analyzed. Alternatively, the segregation of the water-sample can also be made automatically by using an appropriate valve which conducts air into the sample-line after the defined water-sample volume is sucked.

If the key-reagent is, seen from the inlet opening, positioned before the measuring section, the water-sample is mixed with the key-reagent by flowing from the inlet opening toward the measuring section.

If the key-reagent is positioned between the measuring section and the pump opening, the water-sample can be first pumped to the measuring section to determine in a first step a background value with the analyzer. The water-sample can thereafter be pumped to the section between the measuring section and the pump opening to react with the key-reagent, and subsequently pumped backwards to the measuring section to quantitatively determine the analyte in the water-sample.

On the way from the inlet opening towards the measuring section, the water-sample is mixed with the key-reagent in the sample-line. This can be provided, for example, by a relatively long mixing section between the key-reagent position and the measuring section. The homogenous mixing can also be intensified by pumping the mixture repeatedly back and forth through the sample-line.

The key-reagent reacts with the analyte in the water-sample so that the optical and electrochemical properties of the water-sample change. Referring to the example of a photometrical analyzer, the absorption spectra of the water-sample changes particularly at defined spectra lines or defined spectra areas, respectively. The treated and mixed water-sample is measured in the measuring section by the analyzer in the basic unit electrically or optically.

The result of the measurement is evaluated and, when necessary, displayed and/or saved. As soon as the result is obtained, the test-element can be removed manually or automatically.

The test-element can have a size of a flat match stick so that the sample-line can have a corresponding small cross-section, which is in a range between 0.01 $mm^2$ and some square millimeters. The photometrical section or the measuring track, respectively, should be as long as possible, for example, in the range of some millimeters to some centimeters. Therefore, the volume of the water-sample in the photometrical section is in the range of one to circa fifty cubic millimeters. According to the dimensions, the amount of the key-reagent is small so that the potential danger for health and environment is also small. As a consequence, the need for an appropriate disposure can be avoided so that a considerable effort for appropriate disposure or recycling to the distributor or producer, respectively, is avoided.

All steps which are relevant for the quality of the measurement results of the water analysis, such as the dosage of the key-reagent, the mixing of the key-reagent with the water-sample and the waiting for the reaction time etc., are performed semi- or full-automatically, respectively, and air-tight. Errors and hazards resulting from inaccurate handling can therefore be almost completely excluded.

In an embodiment of the present invention, the disposable test-element can be provided with a bottom part and a separate cover part, whereby both parts form the sample-line therebetween. For instance, the bottom part is made out of plastic via injection die-casting whereby the bottom part is provided with an open U-shaped groove. The cover part can, for example, be a clear-transparent plastic film which is adhered or welded to the bottom part after all the reagents and substances have been inserted into the sample-line. The two-part embodiment of the test-element allows for a precise placement of the reagents and substances into the sample-line. This is especially so because the cross-section of the sample-line are a maximum of several square millimeters.

In an embodiment of the present invention, the analyzer can, for example, be a photometer with a light source for generating a measurement beam and a light detector for receiving the measurement beam, whereby the measuring section which is passed through by the beam is formed by a photometer section. The photometer can, for example, be provided as a transmission-photometer. A transmission-photometer has, compared with a reflection-photometer, a better information signal. The transmission-photometer allows a more precise quantitative determination of an analyte at a relative short measuring track. The measuring section is provided with at least one photometrical-window for the inlet and the outlet of the measuring beam. With the photometrical method, different ions, for example, chlorine, phosphate and ammonium, can be measured.

The analyzer can alternatively be an electrochemical analyzer which determines an electrical parameter in the measuring section. The measuring section is provided with at least one electrode or sensor area, respectively, which is connected through electric lines with contacts or contact areas of the test-element, respectively. The contacts of the test-element are connected with the basic unit through contacts or through contact areas, respectively, and therefore with the analyzer of the basic unit. The electrode or sensor area, respectively, has an area of some square micrometers to some millimeters. Different parameters, such as conductivity, redox potential, pH-value and oxygen content, can be measured with the electrochemical method.

The analyzer is alternatively able to measure turbidity or scattering, respectively.

The basic unit can be provided with a photometrical, an optical or an electrochemical analyzer, respectively, so that photometrical, optical and also electrochemical test-elements can be used alternatively via the basic unit.

In an embodiment of the present invention, the measuring track of the measuring section can, for example, be formed by a longitudinal section of the sample-line. The measuring track is thereby arranged in longitudinal direction, not in a cross direction. In this way, the measuring track is much longer as it would be the case if the measuring track would be in cross direction. The longer the measuring section, the more precise the measurement.

The test-element can be provided with a positioning element, which provides an exact positioning of the test-element in the basic unit. The measuring section of the test-element should be exactly in line with the photometer of the basic unit to provide a photometrical measurement without errors. The test-element can therefore be provided with at least one separate positioning element, which provides the positioning in addition to the lateral surface of the test-element in the basic unit. The test-element can, for example, comprise a groove, a cavity or an opening in which a respective snap element of the basic unit snaps in, to position and fix the test-element into the basic unit.

The key-reagent can, for example, be provided in a dry state in the sample-line.

In an embodiment of the present invention, the sample-line can be provided with an auxiliary-reagent in addition to the key-reagent. The auxiliary-reagent can be arranged between the inlet opening and the measuring section or between measuring section and pump opening, depending on the function.

The auxiliary-reagent can, for example be an activator which activates the key-reagent once the auxiliary-reagent is mixed with the water-sample. This can improve the durability, the non-hazardous and/or the insensibility abilities of the key-reagent.

The auxiliary-reagent can be a separate reagent which serves to analyze a second analyte in the water-sample. The auxiliary-reagent can cause a multi-stage reaction based on or after the key-reagent has reacted with the water-sample. The support-reagent can also be an analyte-standard, which, for example, can be used to perform a standard addition.

The auxiliary-reagent can also be a neutralization-reagent which can be arranged between the measuring section and the pump opening. After the water-sample has been analyzed in the measuring section, the water-sample can be pumped to the auxiliary-reagent which reacts with the key-reagent so that the key-reagent is neutralized.

The auxiliary-reagent can also gelatinize and/or color the water-sample after the water-sample has been analyzed. Changing the color of the water-sample shows the customer that the test-element is used. Gelatinizing caused a fixation of the water-sample in the sample-line so that leakage is avoided.

It is also possible to arrange numerous of different reagents in series in the sample-line to analyze different analysts of the same water-sample. Once the water-sample arrives at the respective reagent, the reagent can be dissolved in the water-sample so as to react with the analyte, for example, by changing the color. The analyte can be determined in the measuring section and subsequently, the water-sample can be mixed with the second reagent to determine a second analyte in the water-sample.

In an embodiment of the present invention, the test-element can be provided with a pump-membrane which seals the pump opening fluid-tight and gas-tight, whereby the pump-membrane encloses a pump volume which can be higher than the total pump-channel volume. This allows a precise transport and placement of the water-sample with only one stroke of the pump-membrane at the complete length of the sample-line. The pump-membrane can be controlled via the pump actuator of the basic unit, whereby the pump actuator can be provided with a rod which pushes the pump-membrane. For example, by pushing the rod, the water-sample can be pumped backwards in direction to the inlet opening and by pulling the rod, the water-sample can be pumped forward in direction to the pump opening.

In an embodiment of the present invention, the pump actuator can, for example, be a part of the sample-pump whereby the sample-pump is connected with the pump opening of the inserted test-element. All movable parts of the sample-pump can be arranged at the basic unit. The basic unit and/or the test-element can provide an elastic seal in the pump opening section which provides a sealed connection between the pump opening and the sample-pump. A gas-tight and fluid-tight connection between the pump opening and the sample-pump allows for an accurate and fail-safe operation. An elastic seal provides a sealed fluidic connection between the sample-pump and the sample-line of every test-element. This embodiment provides an accurate and fail-safe analyzing operation even after a long life time and after many measurements.

The test-element can be provided as a multi-analyte-test-element with two separate sample-lines with different key-reagents so that the test-element is able to analyze two or more different analysts. The test-element comprises, for each analyte, a complete analyzing-mimic which comprises a sample-line with an inlet opening, a measuring section and a respective key-reagent. This allows the determination of numerous analysts with only one measurement.

The test-element can be provided as a stripe. The stripe shaped test-element can, for example, be made out of an elongated and flat casting-component in which the sample-line and the measuring section is formed as a groove. The groove which forms the sample-line can be filled with the key-reagent before the stripe is closed by a clear-transparent plastic film.

The photometer window(s) of the photometrical section can be made out of a separate transparent window. The elongated and flat casting-component can alternatively be completely made out of a transparent plastic.

It is also possible to arrange numerous of the test-elements in a removable cartridge which can be inserted into the basic unit. The cartridge can, for example, have the shape of a drum with numerous drum chambers, whereby each drum chamber houses a test-element which is inserted air-tight. The removable cartridge allows the use of numerous test-elements in line by using an appropriate manual, semiautomatic or fully automatic load and unload mechanism.

In an embodiment of the present invention, an absorption body can, for example, be arranged between the measuring section and the pump opening. The absorption body serves to absorb the water-sample after the measurement has been finished and the sample has been pumped to the absorption body. The water-sample is thereby immobilized and a leakage of the water-sample is avoided. The absorption body can, for example, be a fleece body, a clay body like bentonite or can be a so called super-absorber. The body can additionally comprise a neutralizing reagent.

In an embodiment of the present invention, the sample-line can, for example, be provided with a sample filter which filters the water-sample which is sucked through the inlet opening of the test-element. The filtration can be performed before the water-sample is transported to the measuring section to be measured. The sample filter can be made of mineral wool.

According to an embodiment of the present invention, the basic unit can be provided with a heating and/or cooling element to heat or to cool the test-element. The heating or cooling can be controlled so that an adjustment of the temperature of the test-element is possible. A temperature of, for example, 40° C. can significantly accelerate the reaction of the key-reagent with the analyte in the water-sample or can stabilize the reaction, respectively. A cooling of the test-element or the water-sample in the sample-line of the test-element, respectively, reduces the outgassing or the formation of disturbing gas bubbles which can cause errors during photometrical measurements.

In an embodiment of the present invention, the sample-line can be provided with a hydrophobic stopper capillary. The stopper capillary can be arranged close to the pump opening so that the stopper prevents the transportation of the water-sample through the pump opening into the basic unit.

According to an embodiment of the present invention, the sample-line can be provided with a dose capillary arranged between the inlet opening and the measuring section. The dose capillary can, for example, be arranged adjacent to the inlet opening. By using a dose capillary, the water-sample can be sucked, basically by the capillary force, into the test element so that a defined water-sample volume can be segregated. The water-sample can thereafter be pumped repeatedly forth and back inside the sample-channel by using the pump actuator.

The reagent can be arranged adjacent to the inlet opening to prevent an interaction of unreacted analyte with the sample-line wall. This is reasonable for the determination of chlorine, if the test-element or the sample-line wall is made of plastic.

The test-element can be provided with a drying agent to protect the key-reagent against humidity. For example, the drying agent can be separated in the sample-line by using a hydrophobic stopper capillary, whereby the humidity can flow through the stopper capillary to the drying agent.

The inlet opening and/or the pump opening can be sealed with a humidity-tight transport-seal, which can be opened manually or automatically by inserting the test-element into the basic unit, for example, by piercing. Alternatively or additionally, the single test-element can be sealed in a humidity-tight package.

Figure 1:
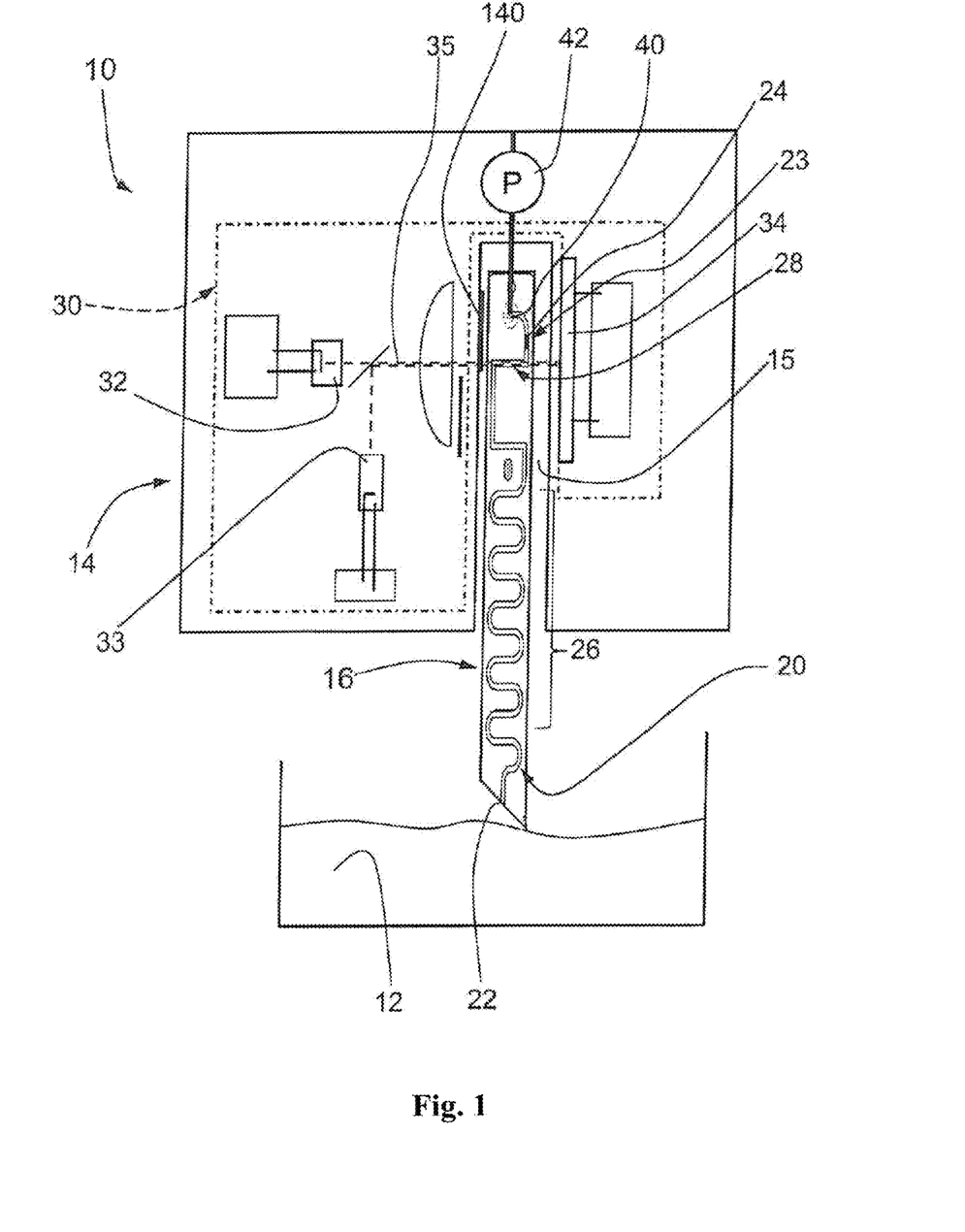
FIG. 1 shows a schematic drawing of a mobile water-analyzing system comprising a basic unit and a test-element.
Figure 3:
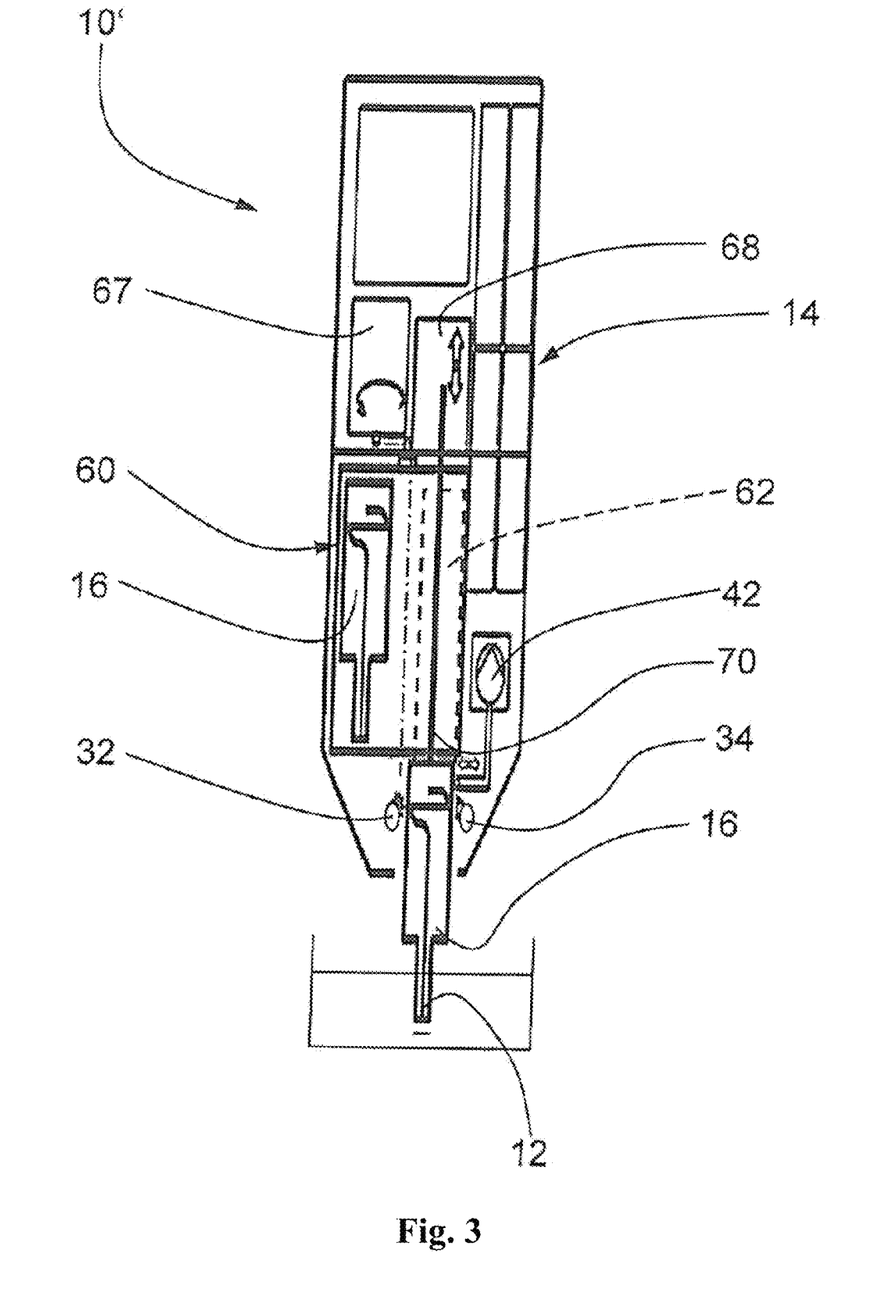
FIG. 3 shows an embodiment of a mobile water-analyzing system including a removable cartridge with several test-elements.
Figure 4:
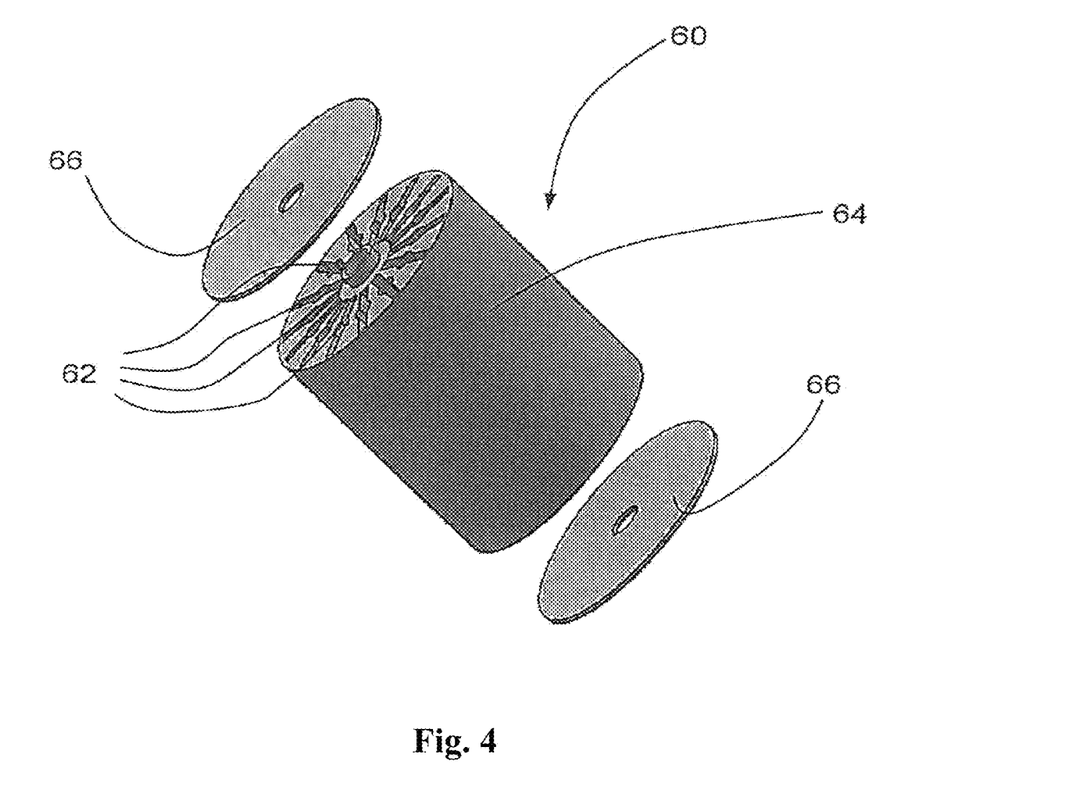
FIG. 4 shows the removable cartridge of FIG. 3.

FIG. 1 and FIG. 3 schematically show a mobile water-analyzing system 10, 10' for a quantitative determination of an analyte in a water-sample. With the described embodiment of a photometrical analyzing system 10, 10' chlorine, phosphate or ammonium can be determined. Alternatively or additionally, the analyzing system can be provided as an electrochemical analyzing system.

The analyzing system of FIG. 1 comprises a basic unit 14 and a removable disposable test-element 16, which is presently inserted into the basic unit 14.

The test-element 16 is provided with a test-element body 18 made out of plastic. The test-element body 18 has a sample-line 20 which is formed as a groove. The side with the groove opening of the test-element body 18 is closed with a transparent plastic film or aluminum cover, respectively (not shown).

The sample-line 20 is provided with an inlet opening 22 which is positioned at the distal referring to the basic unit 14 and through which a water-sample is sucked from a water-reservoir 12. The distal area of the sample-line 20 is provided with a dry key-reagent 24 arranged in the sample-line 20. Adjacent to and, in the flow direction, behind the key-reagent 24 is a meander like mix section 26 of the sample-line 20 in which the key-reagent 24 and the sucked water-sample are mixed homogeneously.

Figure 2:
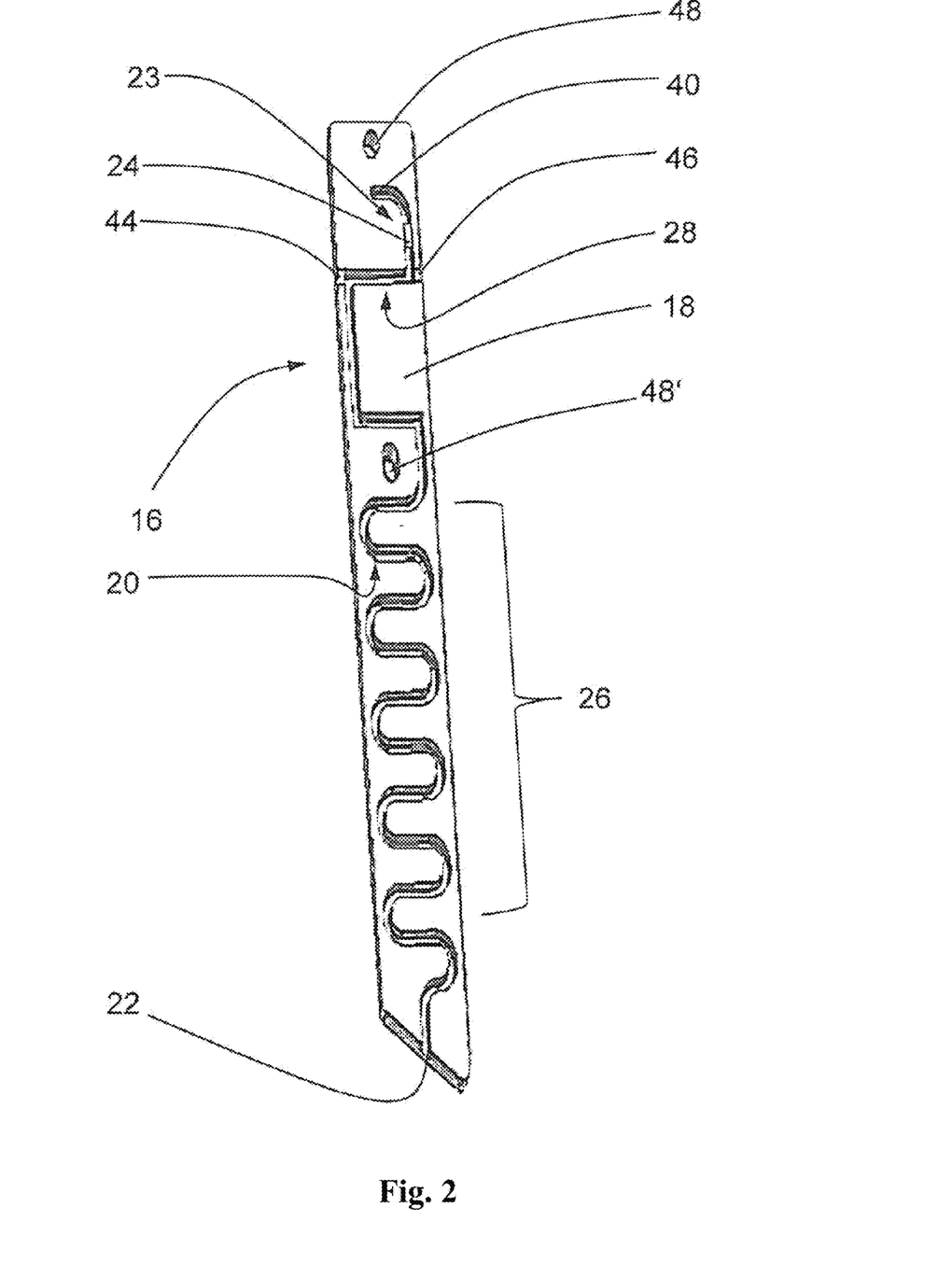
FIG. 2 shows the test-element of the water-analyzing system of FIG. 1.

Adjacent to the mix section 26 is a measuring section 28 in which the analyte is determined quantitatively. The present measuring section 28 is a photometrical section, whereby the measuring section 28 forms a measuring track for the respective photometrical analyzer 30 of the basic unit 14. Both sides of the measuring section 28 comprise a clear-transparent photometrical window 44, 46 as shown in FIG. 2. The test-element body 18 can be completely made out of a clear transparent plastic which allows the measuring beam 35 to pass the measuring section 28. The measuring track of the measuring section 28 is formed by a linear longitudinal section of the sample-line 20, i.e., the measuring track is running along an imaginary longitudinal axis of the sample-line 20 in the measuring section 28. This provides substantially much longer measuring track as it would be the case, if the track would run in cross-direction through the sample-line 20.

At the sample-line end opposite to the inlet opening 22, a pump opening is provided 40 which is connected with a pump actuator of the sample pump of the basic unit when the test-element is inserted.

The basic unit 14 is provided with an analyzer 30 which is a transmission photometer with two light sources 32, 33 and a light detector 34. The light-sources 32, 33 emit light of different wavelengths.

Figure 7:
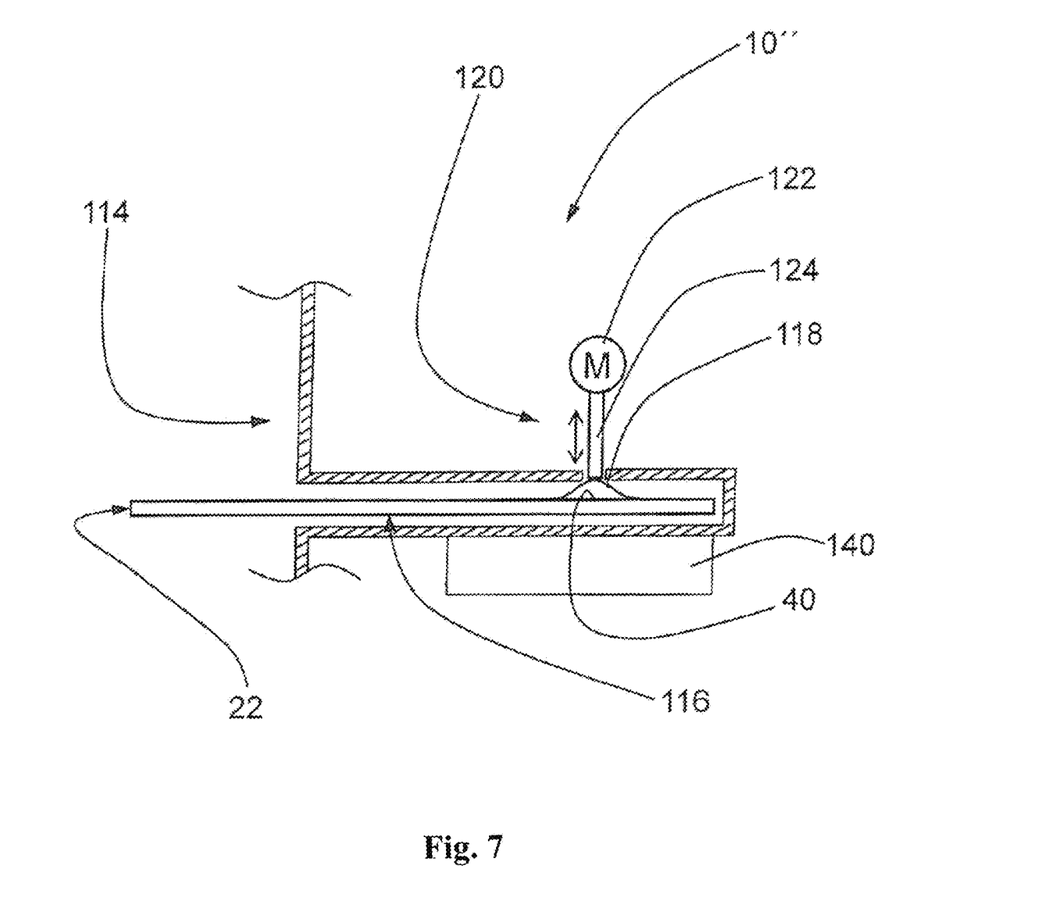
FIG. 7 shows a side view of an embodiment of a test-element with a pump membrane, which is controlled via a pump actuator from the basic unit.

The basic unit 14;114 is furthermore provided with a heat and cooling element 140 which is a peltier-element and is used to heat or to cool the test-element (FIG. 7). The heating or cooling is controlled, so that a constant temperature of the test-element 16;116 is adjusted. A temperature of, for example, 40° C. can significantly accelerate the reaction between an analyte in the water-sample and a key-reagent 24, or can stabilize the reaction, respectively. A cooling of the test-element 16 or the water-sample in the sample-line 20 of the test-element, respectively, reduces the outgassing or the formation of disturbing gas bubbles which cause errors during photometrical measurement.

The test-element 16 is provided with two positioning elements 48, 48' which are realized as openings. The positioning element 48, 48' cooperates with a respective snap element of the basic unit 14 so that the test-element 16 is fixed reproducibly and exactly. This provides that the measuring beam 35 generated by the light source 32, 33 is exactly in line with the photometrical measuring section 28. The test-element receptacle of the basic unit 14 is formed as a slot 15 in which the test-element 16 fits without any clearance.

FIG. 3 shows an embodiment of a mobile water-analyzing system 10' including a removable cartridge 60 which is formed as a drum with 15 drum chambers 62, whereby each drum chamber 62 carries a test-element 16. The plastic drum body 64 is sealed axially with a circular sealing foil 66 so that the chambers 62 are sealed gas-tight and fluid-tight.

As showed in FIG. 3, the removable cartridge 60 is inserted into a respective cartridge slot of the basic unit 14'. The basic unit 14' is provided with a cartridge rotary actuator 67 and a test-element shifter 70. The shifter 70 can shift a test-element 16 automatically from a chamber 62 into the measuring position as shown in FIG. 3.

As soon as the measurement is finished, the shifter 70 moves the test-element 16 out of the measuring position and ejects it out of the basic unit 14'. In a next step, the shifter 70 is completely removed from the cartridge 60. The rotary actuator 67 then turns the cartridge 60 by one chamber angle so that the next chamber 62 with the test-element 16 is in line with the shifter 70. As soon as a measurement request is signalized by the customer, the shifter 70 moves the test-element 16 from the chamber 62 into the measuring position so that the measurement can start.

Figure 5:
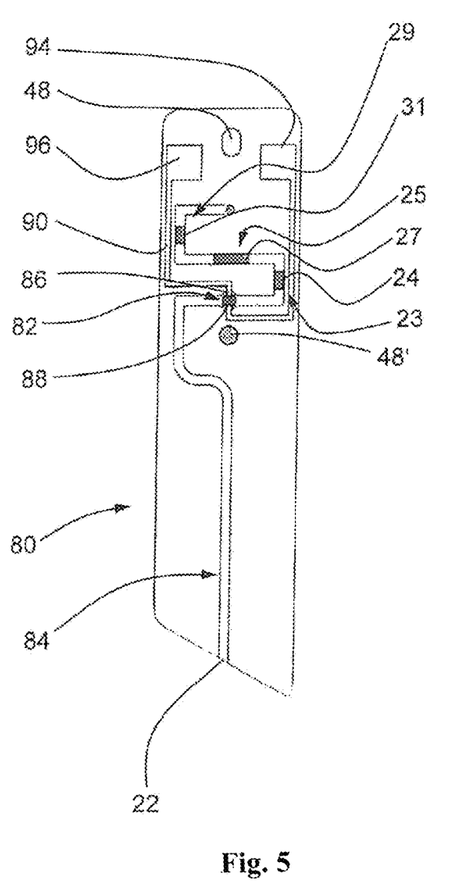
FIG. 5 shows a front view of an embodiment of an electrochemical test-element.
Figure 6:
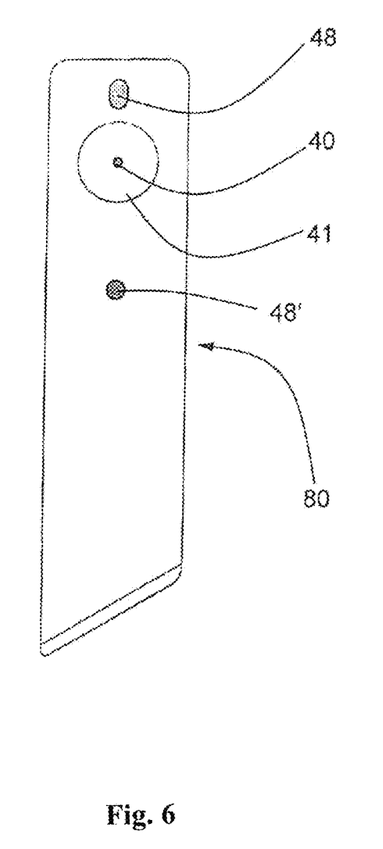
FIG. 6 shows a rear view of the test-element of FIG. 5.

FIG. 5 and FIG. 6 show the respective front view and the rear view of two embodiments of a test-element 80. The test-element 80 is an electrochemical test-element which is provided with an electrochemical measuring section 82 in the sample-line 84. The measuring section 82 is provided with two electrodes 86, 88 in positioned opposed to each other, the electrodes being connected through electric lines 90, 92 with contacts 94, 96. The contacts 94, 96 are arranged in line to respective contacts of the basic unit whereby the contacts are connected with the electrochemical analyzer of the basic unit.

The rear view of the test-element in FIG. 6 shows the pump opening 40. A circular seal element 41 is provided surrounding the pump opening 40 to provide a vacuum-tight connection between the sample-line 84 and a sample-pump realized as a pump actuator 42.

FIG. 7 schematically shows a side view of a part of an embodiment of a mobile water-analyzing system 10". The water-analyzing system 10" is provided with a disposable test-element 116 which is provided with a convex and vesicular pump membrane 118 above the pump opening 40. The pump element which is formed as a pump membrane 118 has a pump volume which is higher as the total volume of the sample-line 84.

The basic unit 114 is provided with a pump actuator 120 with a motor 122 whereby the pump actuator 120 controls a rod 124. The rod 124 pushes against the pump membrane 118 of the inserted disposable test-element 116. The water-sample can be moved over the complete length of the sample-line forward and backward by the rod 124 deforming the pump membrane 118.

To determine an analyte in a water-sample, first a test-element 16 is inserted into the test-element receptacle 15 of the basic unit 14. This can, if given, activate the basic unit 14. In a next step, the inlet opening 22 of the test-element is immersed manually into the analyzing water-reservoir 12 so that the sample-pump 42 sucks a water-sample into the measuring section 28 of the sample-line 20. The analyzer 30 determines the background signal of the water-sample in the measuring section.

As soon as the background signal determination is finished, the water-sample is pumped forward from the measuring section 28 into the reagent section 23. The water-sample meets with the key-reagent 24 in the reagent section 23 so that the key-reagent 24 is mixed with the water-sample. The key-reagent 24 reacts with the analyte in the water-sample so that the optical properties of the water-sample change.

By pumping backwards, the water-sample flows back from reagent section 23 to the measuring section 28. The water-sample is analyzed photometrically by the analyzer 30. The result of the measurement is a gross-value. Subtracting the background from the gross-value leads to a net concentration of the analyte in the water-sample.

With the test-element 80 of FIG. 5 and FIG. 6, an even more precise determination of the analyte in a water-sample can be realized by using standard addition. After the determination of the analyte in the measuring section 82, the water-sample is pumped again forward to the section with the support-reagent 25, whereby the water-sample is mixed with the first auxiliary-reagent 27 which forms a first analyte standard.

The water-sample is then pumped backwards from the section with the auxiliary-reagent 25 into the measuring section 82, whereby the water-sample is analyzed again photometrically. The water-sample is transported again forward to the section with the second auxiliary-reagent 29, whereby the water-sample is mixed with the second auxiliary-reagent 31 which forms a second analyte standard. Finally, the water-sample is transported again backwards from the section with the second auxiliary-reagent to the measuring section, whereby the water-sample is measured by the photometer.

Both photometrical analyte standard measurements lead to a concentration-absorption characteristic line which allows an exact determination of the analyte concentration of the water-sample by using the net concentration value.

Figure 8:
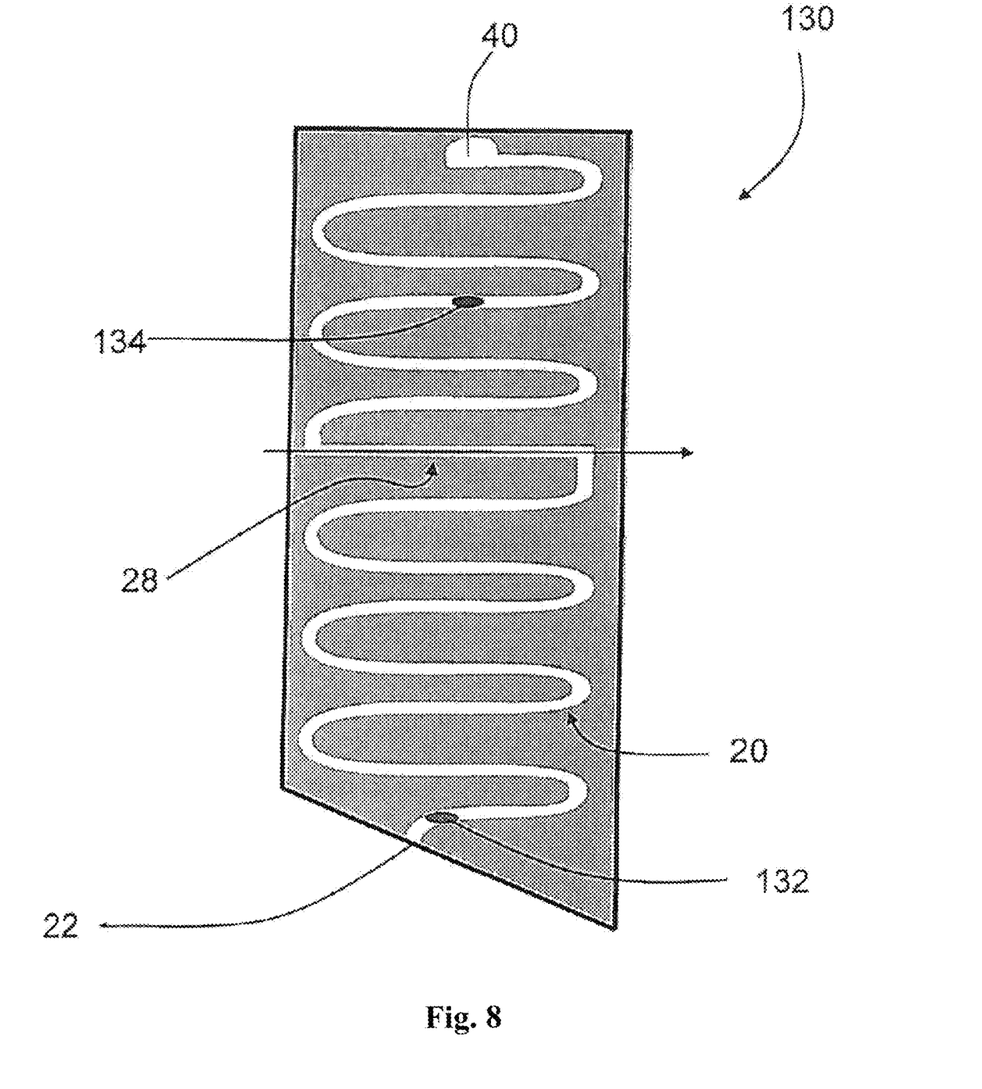
FIG. 8 shows an embodiment of a test-element with a key-reagent and an auxiliary-reagent, whereby both reagents are arranged between an inlet opening and a measuring section.

FIG. 8 shows an embodiment of a test-element 130 in which the key-reagent 132 is arranged close to the inlet opening 22. This positioning of the key-reagent 132 is particularly useful for a chlorine reagent to prevent a reaction of the analyte chlorine with the plastic wall of the sample-line 20. The sample-line 20 or the complete body of the test-element 130, respectively, is made out of a material inert for chlorine, such as polystyrene.

Between the measuring section 28 and the pump opening 40, an auxiliary reagent 134 is provided. The auxiliary reagent 134 can be a separate reagent for analyzing a second analyte in the water-sample. The auxiliary reagent 134 can cause a multi-stage reaction with the water-sample, based on or after the key-reagent 132 has reacted with the water-sample. The auxiliary-reagent 134 can also be an analyte-standard which, for example, can be used to provide a standard addition.

The auxiliary-reagent 134 can also be a neutralization-reagent. After the water-sample has been analyzed in the measuring section 28, the water-sample is transported to the auxiliary-reagent 134, which reacts with the key-reagent 132. The key-reagent 132 is neutralized so that the test-element can be disposed in the community waste.

The auxiliary-reagent 134 can also gelatinize and/or color the water-sample after the water-sample has been analyzed. Changing the color of the water-sample shows the customer that the test-element 130 has been used. By gelatinizing, the water-sample is fixed in the sample-line 20 so that the water-sample cannot leak.

Figure 9:
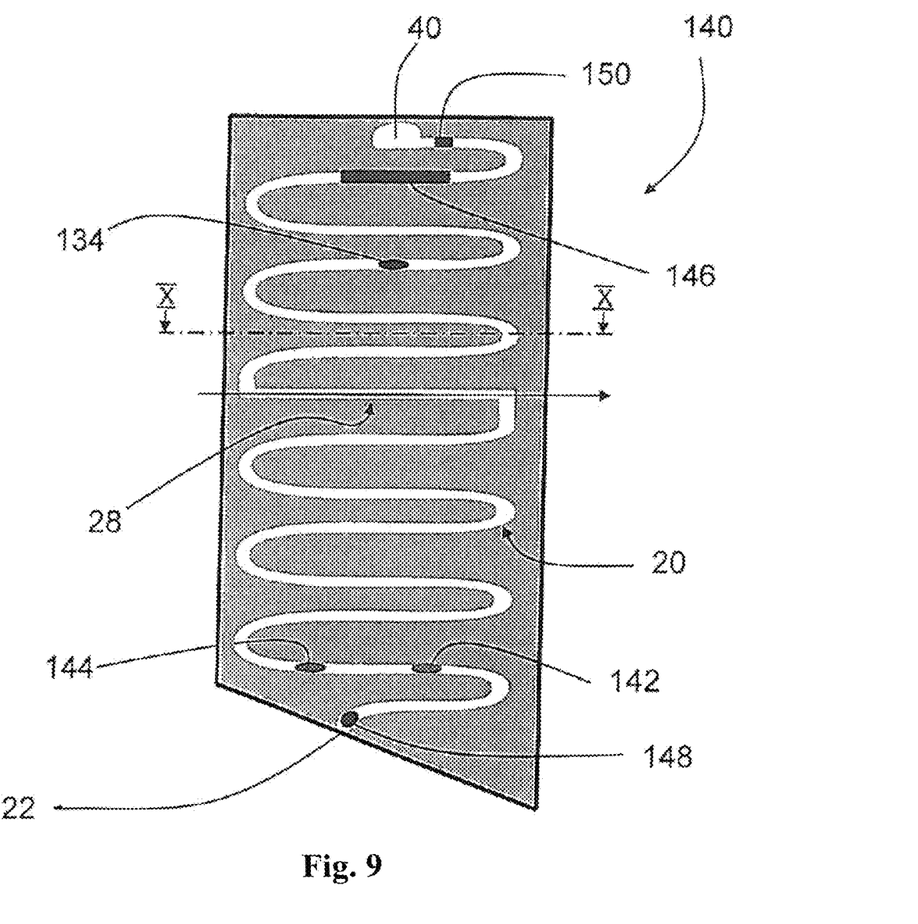
FIG. 9 shows an embodiment of a test-element with a key-reagent and a auxiliary-reagent, whereby both reagents are arranged between a measuring section and a pump opening.

FIG. 9 shows an embodiment of the test-element 140. The key-reagent 142 and the auxiliary-reagent 144 are positioned relatively close to each other between the inlet opening 22 and the measuring section 28. For instance, the auxiliary-reagent 144 is an activator which activates the key-reagent 142 once the auxiliary-reagent 144 is mixed with the water-sample. Both reagents 142, 144 can alternatively be arranged between the measuring section 28 and the pump opening 40.

The sample-line 20 is provided with an absorption body 146 which is a fleece body and is arranged between the measuring section 28 and the pump opening 40. The sample-line 20 is provided with a dose capillary 148 adjacent to the inlet opening 22. Adjacent to the pump opening 40, the sample-line 20 can be provided with a stopper capillary 150 which prevents any leakage out of the sample-line 20. The sample-line 20 is also provided with a sample filter 152 between the inlet opening 23 and the measuring section 28, and in particular close to the inlet opening 23, to filter the sucked water-sample.

Figure 10:
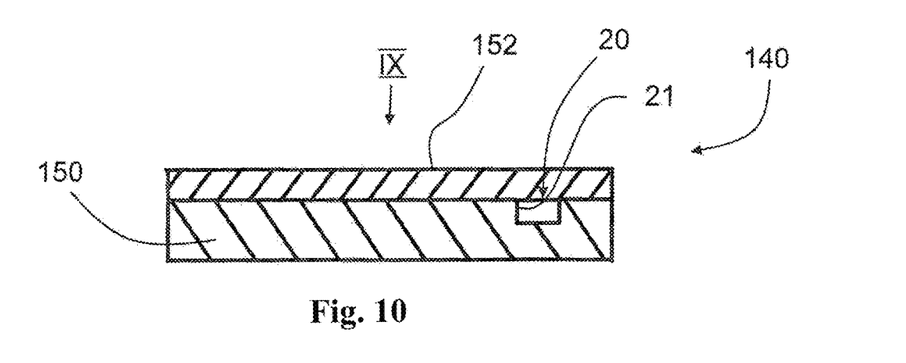
FIG. 10 shows the test-element of FIG. 9 in a cross-sectional view in the X-X direction.

FIG. 10 shows, as an example, a cross section of the test-element 140 of FIG. 9. The test-element 140 comprises basically two parts: a plastic bottom part 150 which is made by injection die-casting and a separate cover part 152 which is a clear-transparent plastic film adhered or welded to the bottom part. The bottom part 150 is, in the cross section, provided with a U-shaped sample-line groove 21 which is closed by the cover part 152. In this way, the bottom part 150 and the cover part 152 form the sample-line 20.

The present invention is not limited to embodiments described herein; reference should be had to the appended claims.

What is claimed is:

1. A test element for a mobile water analyzing system, the test element comprising:
 a test element body comprising a test element body length, a test element body width, and a test element body thickness, the test element body length being greater than the test element body width, and the test element body width being greater than the test element body thickness;
a sample line comprising:
  an inlet opening disposed at a first end, the inlet opening being configured to receive a water sample,
  a pump port disposed at a second end of the sample line,
  an inlet section disposed between the inlet opening and the pump port, and
  a measuring section comprising at least one window arranged at an end of the measuring section within the test element body thickness, the measuring section being arranged between the inlet section and the pump port and being coincident with a sample pathway,
  wherein,
the measuring section is formed by a longitudinal section of the sample line which is arranged perpendicular to the test element body length and parallel to the test element body width; and
a key reagent disposed in the sample line.

2. The test element as recited in claim 1, wherein the sample line is a microfluidic sample line.

3. The test element as recited in claim 1, further comprising a bottom part and a separate cover part, the bottom part and the separate cover part being arranged so as to form the sample line therebetween.

4. The test element as recited in claim 1, further comprising at least one contact, and at least one electrode arranged in the measuring section, wherein the at least one electrode is configured to connect with an analyzer via the at least one contact and via at least one contact of a separate basic unit.

5. The test element as recited in claim 1, wherein, during a photometric measurement with a measurement beam, the measurement beam is aligned with the measuring section so that the photometric measurement occurs along the measuring section and not in a cross direction thereto.

6. The test element as recited in claim 1, further comprising a pump membrane configured to be controlled by a pump actuator.

7. The test element as recited in claim 6, wherein the pump actuator is a part of a sample pump of a separate basic unit, the sample pump being connected with the pump port.

8. The test element as recited in claim 1, wherein the test element further comprises an auxiliary reagent disposed in the sample line, the auxiliary reagent being disposed between the key reagent and the pump port.

9. The test element as recited in claim 1, wherein test element further comprises an absorption body disposed between the measuring section and the pump port.

10. The test element as recited in claim 1, wherein test element further comprises a sample filter disposed in the inlet section.

11. The test element as recited in claim 1, wherein test element further comprises a hydrophobic stopper capillary disposed in the sample line.

12. The test element as recited in claim 1, wherein the test element further comprises a dose capillary disposed in the sample line.

13. The test element as recited in claim 1, wherein test element is prefabricated.

14. A test element for a mobile water analyzing system comprising a photometer, the test element comprising:
a test element body comprising a test element body length, a test element body width, and a test element body thickness, the test element body length being greater than the test element body width, and the test element body width being greater than the test element body thickness;
a microfluidic sample line comprising:
  an inlet opening disposed at a first end, the inlet opening being configured to receive a water sample,
  a pump port disposed at a second end of the sample line,
  an inlet section disposed between the inlet opening and the pump port, and
  a measuring section formed by a longitudinal section of the microfluidic sample line, the measuring section comprising at least one window arranged at an end of the measuring section within the test element body thickness, the measuring section being arranged between the inlet section and the pump port and being coincident with a sample pathway; and
a key reagent disposed in the microfluidic sample line, wherein,
during a photometric measurement with a measurement beam, the measurement beam is aligned with the measuring section so that the photometric measurement occurs along the measuring section and not in a cross direction thereto, and
the measuring section is formed by a longitudinal section of the sample line which is arranged perpendicular to the test element body length and parallel to the test element body width.

15. The test element as recited in claim 1, wherein the key reagent disposed in the sample line is provided in a dry state.

* * * * *